US00PP17809P2

(12) United States Plant Patent
Eskelund Hansen

(10) Patent No.: US PP17,809 P2
(45) Date of Patent: Jun. 12, 2007

(54) ROSE PLANT NAMED 'EVERA 141'

(50) Latin Name: *Rosa hybrida*
Varietal Denomination: Evera 141

(75) Inventor: Rosa Eskelund Hansen, Fåborg (DK)

(73) Assignee: Roses Forever ApS, Fåborg (DK)

( * ) Notice: Subject to any disclaimer, the term of this patent is extended or adjusted under 35 U.S.C. 154(b) by 0 days.

(21) Appl. No.: 11/323,162

(22) Filed: Dec. 30, 2005

(51) Int. Cl.
*A01H 5/00* (2006.01)

(52) U.S. Cl. ..... Plt./108

(58) Field of Classification Search ..... Plt./108
See application file for complete search history.

*Primary Examiner*—Kent Bell
(74) *Attorney, Agent, or Firm*—C. A. Whealy

(57) ABSTRACT

A new and distinct cultivar of rose plant named 'Evera 141', characterized by its upright and rounded plant habit; dark green-colored leaves; freely flowering habit; large fully double red-colored flowers; flowers held upright on strong and erect peduncles; and good postproduction longevity.

1 Drawing Sheet

Botanical designation: *Rosa hybrida.*
Cultivar denomination: 'Evera 141'.

BACKGROUND OF THE INVENTION

The present invention relates to a new and distinct cultivar of the Rose class, botanically known as *Rosa hybrida,* commercially known as a potted Rose and hereinafter referred to by the name 'Evera 141'.

The new Rose plant is a product of a planned breeding program conducted by the Inventor in Denmark. The objective of the breeding program was to develop new potted Rose cultivars with novel and attractive flower colors, disease resistance and excellent postproduction longevity.

The new Rose plant originated from a cross-pollination made by the Inventor on Mar. 1, 2003 of two unnamed proprietary *Rosa hybrida* seedlings, not patented. The cultivar Evera 141 was discovered and selected by the Inventor as a flowering plant within the progeny of the stated cross-pollination in a controlled environment in Denmark. Plants of the new cultivar differ primarily from plants of the parent selections primarily in flower color.

Asexual reproduction of the new Rose plant by cuttings in Denmark since Feb. 10, 2004, has shown that the unique features of this new Rose plant are stable and reproduced true to type in successive generations of asexual reproduction.

SUMMARY OF THE INVENTION

The new Rose plant has not been observed under all possible environmental conditions. The phenotype may vary significantly with variations in environment such as temperature and light level, without, however, any variance in genotype.

The following traits have been repeatedly observed and are determined to be the unique characteristics of 'Evera 141'. These characteristics in combination distinguish the new Rose plant as a new and distinct cultivar:

1. Upright and rounded plant habit.
2. Dark green-colored leaves.

3. Freely flowering habit.
4. Large fully double dark red-colored flowers.
5. Flowers held upright on strong and erect peduncles.
6. Good postproduction longevity.

Plants of the new Rose plant can be compared to plants of the Rose cultivar Evera 103, disclosed in U.S. Plant Pat. No. 16,780. In side-by-side comparisons conducted in Denmark, plants of the new Rose differed from plants of the cultivar Evera 103 in the following characteristics:

1. Plants of the new Rose were more freely flowering than plants of the cultivar Evera 103.
2. Plants of the new Rose had smaller flowers with twice as many petals per flower than plants of the cultivar Evera 103.
3. Plants of the new Rose and the cultivar Evera 103 differed in flower coloration as plants of the cultivar Evera 103 had yellow orange-colored flowers.

BRIEF DESCRIPTION OF PHOTOGRAPHS

The accompanying colored photographs illustrate typical specimens of the vegetative growth and flowers of the new Rose plant, showing the colors as true as it is reasonably possible to obtain in colored reproductions of this type. Colors in the photographs may differ slightly from the color values cited in the detailed botanical description which accurately describe the actual colors of the new Rose plant.

The photograph at the top of the sheet comprises a side perspective view of typical plants of the new Rose plant grown in a container.

The photographs at bottom of the sheet comprises a close-up view of a typical plant of the new Rose plant.

DETAILED BOTANICAL DESCRIPTION

The aforementioned photographs and following observations and measurements describe plants grown in Denmark in 10.5-cm containers in a glass greenhouse and under conditions which closely approximate commercial production conditions during the summer. Plants used for the description were about 15 weeks old when the photographs and description were taken. In the following description, color references are made to The Royal Horticultural Society Colour Chart, 2001 Edition, except where general terms of ordinary dictionary significance are used.

Classification:

*Botanical.*—*Rosa hybrida* cultivar Evera 141.

*Commercial.*—Potted Rose.

Parentage:

*Female, or seed, parent.*—Unnamed proprietary seedling, not patented.

*Male, or pollen, parent.*—Unnamed proprietary seedling, not patented.

Propagation:

*Type.*—Terminal or stem cuttings.

*Time to rooting.*—8 to 10 days with soil temperatures of 20° C.

*Root description.*—Fine; freely branching.

Plant description:

*Form.*—Upright and rounded plant habit.

*Plant height.*—About 20 cm.

*Plant width.*—About 14 cm.

*Growth habit.*—Moderately vigorous; suitable for 10.5-cm containers.

*Stem description.*—Branching habit: About three to five lateral branches per plant. Lateral branch length: About 14 cm to 18 cm. Lateral branch diameter: About 5 mm. Internode length: About 2 cm. Texture: Smooth, glabrous. Color: 146B. Thorns: Quantity: Sparse. Length: About 3 mm to 5 mm. Diameter: About 5 mm. Shape: Roughly deltoid. Color, immature: Close to 160D. Color, mature: Close to 164B.

*Foliage description.*—Arrangement: Alternately; compound with typically three to five leaflets per leaf, generally symmetrical. Leaf length: About 7 cm to 8 cm. Leaf width: About 5 cm to 6 cm. Leaflet length: About 2.2 cm to 3.5 cm. Leaflet width: About 1.2 cm to 2 cm. Shape: Ovate. Apex: Acuminate. Base: Obtuse. Margin: Serrulate. Venation pattern: Pinnate; reticulate. Texture, upper and lower surfaces: Smooth, glabrous; leathery. Petiole length: About 1.4 cm to 3 cm. Petiole diameter: About 1 mm. Petiole texture, upper and lower surfaces: Smooth, glabrous. Color: Developing foliage, upper surface: 137B; margin, 185C. Developing foliage, lower surface: 191B; margin, 185C. Fully expanded foliage, upper surface: Darker than 137A. Fully expanded foliage, lower surface: 191A. Venation, upper surface: 146A. Venation, lower surface: 146D. Petiole, upper and lower surfaces: Darker than 146A. Stipules: Shape: Lanceolate; apex, acuminate; base, truncate; margin, serrate. Length: About 3 mm to 4 mm. Width: About 0.8 mm. Texture, upper and lower surfaces: Leathery, smooth. Color, upper surface: Close to 137A. Color, lower surface: Close to 137B to 137C.

Flower description:

*Flower type and habit.*—Large fully double red-colored flowers. Consistently symmetrical rosette flowers that are hemispherical in shape. Flowers borne singly on erect and strong peduncles. Freely flowering habit, one to five flower buds and flowers per lateral branch. Flowers persistent.

*Flowering season.*—Year-round under greenhouse conditions, optimal flowering from spring through autumn under garden conditions; flowering intermittent.

*Flower diameter.*—About 3.5 cm to 4 cm.

*Flower depth (height).*—About 1 cm to 1.5 cm.

*Flower longevity on plant.*—About two weeks.

*Fragrance.*—Strong; typical of *Rosa.*

*Flower buds.*—Shape: Ovoid. Length: About 1.5 cm. Diameter: About 6 mm. Color: 138A to 138B.

*Petals.*—Quantity: About 70 per flower. Length: About 1.3 cm to 1.8 cm. Width: About 0.9 cm to 2.2 cm. Shape: Broadly obovate. Apex: Rounded; retuse. Base: Attenuate. Margin: Entire. Texture, upper and lower surfaces: Smooth, glabrous; satiny. Color: When opening, upper surface: 52A; towards the base, lighter than 52A. When opening, lower surface: 54B; towards the base, lighter than 54B. Fully opened, upper surface: Close to 46C. Fully opened, lower surface: Close to 53D.

*Sepals.*—Quantity per flower: Typically five. Calyx length: About 2.5 cm. Calyx diameter: About 6 mm. Shape: Linear; falcate. Apex: Sharply pointed. Base: Truncate. Texture, upper and lower surfaces: Pubescent. Color, upper and lower surfaces: Close to 137A.

*Peduncles.*—Strength: Moderately strong, but flexible. Aspect: Mostly erect. Length: About 3 cm. Diameter: About 1 mm to 1.5 mm. Texture: Smooth, glabrous. Color: 144A.

*Reproductive organs.*—Stamens: Quantity: About 50 per flower. Anther length: About 1 mm. Anther shape: Oval. Anther color: 163A. Pollen color: Close to 21A to 21B. Pistils: Quantity: About 50 per flower. Pistil length: About 3 mm to 5 mm. Stigma color: 39A to 39B. Style color: Close to 145B. Receptacle shape: Cup-like. Receptacle size: About 4 mm by 5 mm. Receptacle texture: Smooth, glabrous. Receptacle color: Close to 144A.

*Seed/fruit.*—Seed and fruit production has not been observed.

Disease/pest resistance: Plants of the new Rose have not been shown in be resistant to pathogens and pests common to Rose plants.

Temperature tolerance: Plants of the new rose have been shown to be tolerant to temperatures from 0 to 45° C.

It is claimed:

1. A new and distinct rose plant named 'Evera 141', as illustrated and described.

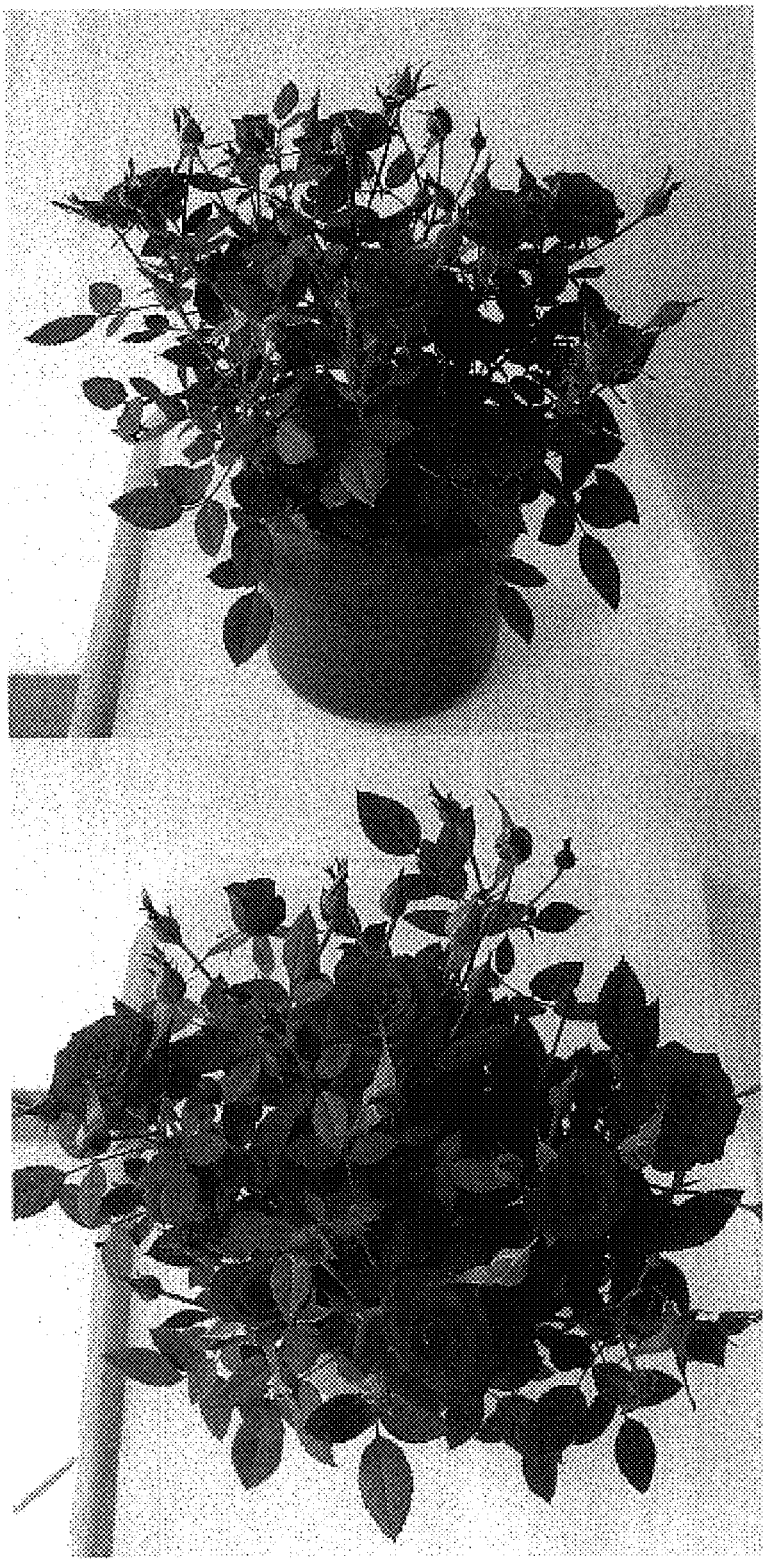

* * * * *